US008540651B2

(12) United States Patent
Pfeffer et al.

(10) Patent No.: US 8,540,651 B2
(45) Date of Patent: Sep. 24, 2013

(54) PHYSIOLOGICAL AND BEHAVIORAL SENSORS AND METHODS

(75) Inventors: Lawrence E. Pfeffer, Lexington, MA (US); Suzanne M. Wendelken, Arlington, MA (US); Adam T. Fulford, Cambridge, MA (US); Andrea K. Webb, Medford, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 12/883,451

(22) Filed: Sep. 16, 2010

(65) Prior Publication Data
US 2012/0071792 A1 Mar. 22, 2012

(51) Int. Cl.
*A61B 5/00* (2006.01)
(52) U.S. Cl.
USPC .......................................... 600/595
(58) Field of Classification Search
USPC ......................... 600/587, 595, 592
See application file for complete search history.

(56) References Cited

U.S. PATENT DOCUMENTS

| 4,195,643 | A | * | 4/1980 | Pratt, Jr. ................. | 600/592 |
|---|---|---|---|---|---|
| 4,598,717 | A | * | 7/1986 | Pedotti ................... | 600/592 |
| 5,677,498 | A | * | 10/1997 | Oakes et al. ............ | 73/862.541 |
| 5,771,261 | A | | 6/1998 | Anbar | |
| 5,964,720 | A | * | 10/1999 | Pelz ....................... | 600/595 |
| 6,030,347 | A | | 2/2000 | Nakamura et al. | |
| 6,505,522 | B1 | | 1/2003 | Wilssens | |
| 6,547,743 | B2 | | 4/2003 | Brydon | |
| 6,821,258 | B2 | * | 11/2004 | Reed et al. ............. | 600/595 |
| 6,840,907 | B1 | | 1/2005 | Brydon | |
| 6,852,086 | B2 | * | 2/2005 | Atlas et al. ............. | 600/595 |
| 7,100,439 | B2 | * | 9/2006 | Carlucci ................. | 73/172 |
| 7,111,980 | B2 | | 9/2006 | Pavlidis et al. | |
| 7,650,803 | B2 | | 1/2010 | Ando et al. | |
| 7,928,967 | B2 | * | 4/2011 | Underwood et al. .... | 345/179 |
| 8,279,057 | B2 | * | 10/2012 | Hirose .................... | 340/517 |
| 2005/0143629 | A1 | * | 6/2005 | Farwell .................. | 600/300 |
| 2007/0191742 | A1 | * | 8/2007 | Park ....................... | 600/587 |
| 2008/0045847 | A1 | | 2/2008 | Farag et al. | |

FOREIGN PATENT DOCUMENTS

JP 2008099849 A 5/2008

OTHER PUBLICATIONS

Azavedo et al, "A freezing-like posture to pictures of mutilation," Psychophysiology, vol. 42, pp. 255-260 (2005).
Benson, "Will airports screen for body signals? Researchers hope so," CNN, 2 pages (Oct. 6, 2009).
Bracha et al, "Does 'Fight or Flight' Need Updating?," Psychosomatics vol. 45:5, pp. 448-449 (Sep.-Oct. 2004).
Bracha, "Freeze, Flight, Fight, Fright, Faint: Adaptationist Perspectives on the Acute Stress Response Spectrum," CNS Spectrums, vol. 9, No. 9, pp. 679-685 (Sep. 2004).

(Continued)

*Primary Examiner* — Max Hindenburg
(74) *Attorney, Agent, or Firm* — Goodwin Procter LLP

(57) ABSTRACT

In various embodiments, a physiological or behavioral signal is derived from a vertical force resulting from the entire weight of a subject. A system for measuring physiological and behavioral signals in a human subject may include a measurement platform for bearing the subject, at least one force sensor for measuring vertical force imparted by an entire weight of the subject, and a signal processor for deriving at least one physiological or behavioral signal, such as a ballistocardiogram, from the measured force. The force sensor(s) may support the measurement platform and be disposed between the measurement platform and a support surface.

23 Claims, 6 Drawing Sheets

(56) References Cited

OTHER PUBLICATIONS

Culpepper, "Design of quasi-kinematic couplings," Precision Engineering, vol. 28, pp. 338-357 (2004).

Hsu, "Are Wii Balance Boards the Future of Airport Security?," Popular Science, 3 pages (Oct. 7, 2009).

Moss, "Ballistocardiographic Evaluation of the Cardiovascular Aging Porcess," Journal of the American Heart Association, Circulation vol. 23, pp. 434-451 (Mar. 1961).

National Academy of Sciences, "The Polygraph and Lie Detection," 416 pages (2003).

Nichols, "Balance Retraining After Stroke Using Force Platform Biofeedback," Physical Therapy, vol. 77, No. 5, pp. 553-558 (May 1997).

Verschuere et al, "Autonomic and behavioral responding to concealed information: Differentiating oreinting and defensive responses," Psychophysiology, vol. 41, pp. 461-466 (2004).

Lafayette Instrument Polygraph "Activity Sensor Seat Pad for Computerized Polygraph" 2009, [online] retrieved on Feb. 11, 2013, <URL: http://www.lafayettepolygraph.com/product_detail.asp?ItemID=1264>.

* cited by examiner

PHYSIOLOGICAL AND BEHAVIORAL SENSORS AND METHODS

STATEMENT REGARDING FEDERALLY SPONSORED RESEARCH

This invention was made with government support under HSHQDC-08-C-00047 and HSHQDC-10-C-00012 awarded by the U.S. Department of Homeland Security. The government has certain rights in the invention.

FIELD OF THE INVENTION

The technology disclosed herein relates generally to physiological and behavioral sensors, and in particular, to sensors for measuring, e.g., ballistocardiograms, that are unobtrusive and require no skin contact.

BACKGROUND

Various physiological (e.g., relating to heart function and/or respiration) and behavioral signals are frequently utilized to provide insight into the nervousness or truthfulness of the subject being monitored. For example, in polygraphy, a subject's fidgeting and/or muscle tensing activity is measured by means of an "activity pad" located on the seat the subject is sitting upon while being questioned by the polygrapher, thus monitoring any attempts by the subject to defeat the host of other sensors to which he/she is physically connected.

One useful physiological signal is the ballistocardiogram (BCG), which is a measure of the mechanical reaction of the human body to the pumping of blood therein. Specifically, the BCG measures mechanical activity of the heart and surrounding tissue, e.g., the impact of blood colliding with portions of the heart and blood vessels, recording the transient forces as minute changes in the weight of the subject. Unfortunately, the utility of BCG has remained quite limited in practice, as accurate measurements typically require the subject to be lying down and strapped to a complicated bed-like apparatus in order to isolate the BCG signal from gravitational effects. BCG measurement systems have even required the subject to hold his/her breath during data acquisition.

For a variety of tasks, including security screening, surveillance, and high-throughput medical screening, the ability to quickly and efficiently measure physiological signals such as the BCG, heart rate, respiration rate, and weight, as well as behavioral signals such as center-of-gravity ("CG") changes, for human subjects would prove quite useful. For example, changes in behavioral signals may indicate nervous jitter (or fidgeting) behavior. Similarly, a sudden decrease in such movements may indicate a behavioral response termed "hypervigilance" or the "freeze response." Furthermore, the ability to make such measurements unobtrusively would facilitate screening throughput (i.e., requiring no delays for subjects to undress or have electrodes placed on their skin) and reduce anxiety, embarrassment, or distraction due to awareness of the measurement system, any of which could influence the quality of the measured data.

SUMMARY

In accordance with various embodiments of the invention, one or more selected physiological and/or behavioral signals are unobtrusively measured. For purposes hereof, an "unobtrusive" measurement is one that does not utilize electrodes contacting the subject, and does not require exposure of any specific area of the subject's skin. The physiological signals can include, e.g., the BCG, weight, and/or respiration rate, and the behavioral signals can include, e.g., measurement of the location of the subject's CG, including metrics based on the magnitude and/or direction of CG movements and their rates of change. The subject may be free-standing, standing with support from a railing or similar structure, or seated. Thus, the subject is generally vertically oriented, at least above the waist, enabling faster and less intrusive measurements to be made on the subject compared to systems requiring the subject to be horizontally oriented.

In various preferred embodiments, physiological signals such as the BCG are measured irrespective of (and/or without concomitant determination of) changes of a subject's CG, e.g., swaying or shifting in position. Thus, accurate measurement of, e.g., BCG may be insensitive to lateral weight shifts and accomplished even when the subject is not completely still.

Measurement systems in accordance with embodiments of the invention typically feature a rigid, substantially horizontal platform that supports the entire weight of the subject. Optionally, a chair, railing, or other support structure may be included, preferably resting entirely on the platform such that no force or weight transmitted thereto by the subject is unmeasured. One or more force sensors support the platform and measure the forces supporting (and/or imposed by) the platform, the subject, and any optional support structure. In various embodiments, a mechanical device such as a bearing is utilized between the platform and each force sensor in order to permit the transmission of forces to the force sensor but prohibit the transmission of torque thereto. One or more ancillary sensors may be utilized to measure (and facilitate compensation for) tilt and/or vibration of the platform during signal acquisition. Finally, a signal processor is utilized to derive the desired physiological and/or behavioral signals from the measured data.

In one aspect, embodiments of the invention feature a system for measuring physiological and behavioral signals in a human subject, which includes or consists essentially of one or more force sensors for measuring vertical force imparted by the entire weight of the subject, as well as a signal processor for deriving a physiological or behavioral signal from the measured force. The force sensor(s) may measure only substantially vertical force. The system may include a structure for supporting the posture of the subject that includes a substantially vertical thorax.

Embodiments of the invention may include one or more of the following, in any of a variety of combinations. The system may include a platform for bearing the subject. The system may include a bearing disposed between each force sensor and the platform, the bearing substantially transmitting vertical force but not torque from the platform to the force sensor. At least three non-collinear force sensors may be disposed proximate the periphery of the platform. A substantially stationary support and/or a chair may be disposed entirely on the platform such that its entire weight is supported by the platform.

The signal processor may include at least one calibration module for calibrating the vertical force, thereby substantially eliminating bias, slope error, hysteresis, and/or non-linearity from the vertical force. The signal processor may include at least one taring module for subtracting from the vertical force the weight contribution from the platform (and/or any support or chair thereon). The system may feature multiple force sensors, and the signal processor may include a summation module for summing vertical force measured by each of the force sensors. The signal processor may include a high-pass filtering module for removing a steady-state component from a total vertical force measured by the force sensor(s). The high-pass filtering module may remove from the total vertical force a spectral component having a frequency below a cardiac frequency of interest (e.g., below approximately 0.5 Hz). The high-pass filtering module may include or consist essentially of a Bessel filter.

The signal processor may include a low-pass filtering module for removing, from the total vertical force measured by the force sensor(s), a spectral component having a frequency above a cardiac frequency of interest (e.g., above approximately 10 Hz, above approximately 30 Hz, or even above approximately 50 Hz). The physiological or behavioral signal may include or consist essentially of a ballistocardiogram. The signal processor may include a centroid-calculating module for determining a center of gravity of the subject based on the measured force. The physiological or behavioral signal may include or consist essentially of jitter and/or hypervigilance.

In another aspect, embodiments of the invention feature a method for measuring physiological and behavioral signals. The vertical force imparted by the entire weight of a human subject having a substantially vertical thorax is measured, and a physiological or behavioral signal is extracted from the measured vertical force. The physiological or behavioral signal may be extracted without sensors attached to the subject.

Embodiments of the invention may include one or more of the following, in any of a variety of combinations. The measured vertical force may be calibrated to substantially eliminate bias, slope error, hysteresis, and/or non-linearity. The subject may be supported by a platform, and the weight contribution of the platform may be subtracted from the vertical force. Extracting the physiological or behavioral signal may include removing from the measured vertical force at least one spectral component having a frequency above or below a cardiac frequency of interest (and/or a range of cardiac frequencies of interest). Extracting the physiological or behavioral signal may include removing from the measured vertical force a steady-state component corresponding to the entire weight of the subject. The physiological or behavioral signal may include or consist essentially of a ballistocardiogram. Extracting the physiological or behavioral signal may include determining a center of gravity of the subject. The physiological or behavioral signal may include or consist essentially of jitter and/or hypervigilance. The vertical force may be measured by multiple force sensors disposed proximate a periphery and supporting a platform, the platform supporting the subject. The subject may be interviewed and/or subjected to a cognitive stimulus while measuring the vertical force.

These and other objects, along with advantages and features of the invention, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means ±10%, and, in some embodiments, ±5%. The term "consists essentially of" means excluding other materials that contribute to function, unless otherwise defined herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
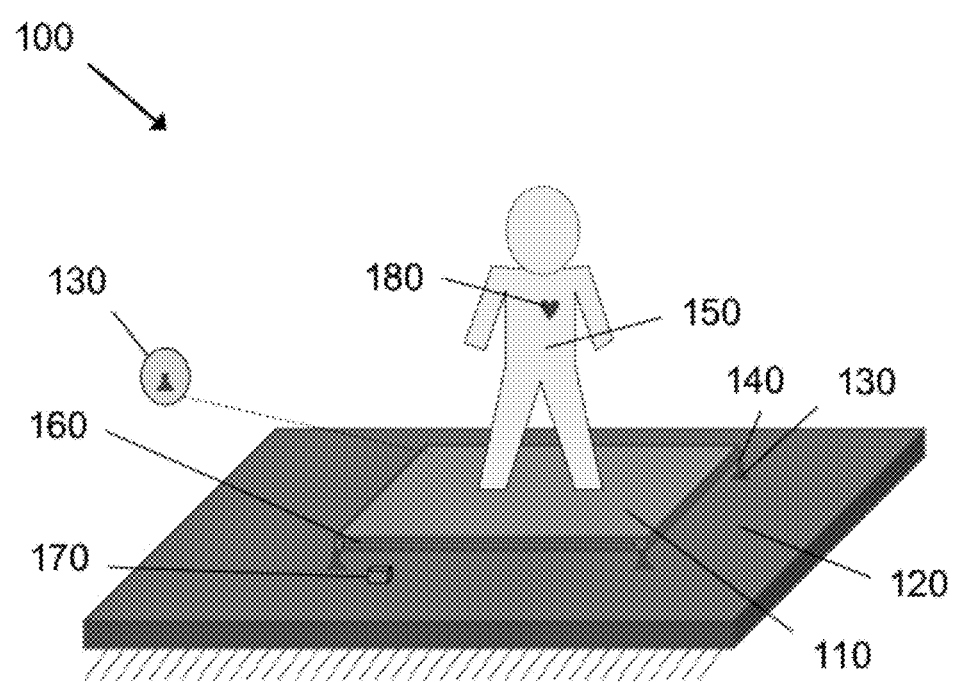
FIGS. 1-3 schematically depict perspective views of various measurement systems for measurement of physiological and/or behavioral signals from a human subject, in accordance with embodiments of the invention.

FIG. 1 depicts a measurement system 100 that includes a rigid, substantially horizontal platform 110, which is supported from a stationary surface 120 by one or more force sensors (i.e., load cells) 130. (Note that, as depicted, one of the force sensors 130 is obscured by platform 110 and is shown schematically offset from its true position.) In an embodiment, the force sensor 130 measures only compressive forces, although force sensors 130 that measure only tensile forces or that measure both tensile and compressive forces may be utilized. Examples of force sensors 130 that may be utilized in various embodiments of the invention include the LGP 382 Compression Only Ultra Precision Load Cell and the LGP 380 Ultra Precision Tension/Compression Load Cell, available from Cooper Instruments & Systems of Warrenton, Va., as well as the SMD 5400, available from Strain Measurement Devices of Wallingford, Conn.

A bearing 140 (or equivalent mechanical device) is preferably disposed between each load cell 130 and the platform 110 such that the forces applied to the platform 110 are transferred through the bearing 140 to load cell 130. The bearing 140 may include or consist essentially of, e.g., a load button or a rod end (e.g., the LBC-012 Load Button or the REC-012M Rod End, available from Omega Engineering of Stamford, Conn.). The bearings 140 transmit vertical forces, but not torques (i.e., moment loads), from the platform 110 to the force sensors 130. Thus, in preferred embodiments, force sensors 130 only measure vertical forces and are substantially insensitive to non-vertical forces or torques. In an embodiment, one or more of the force sensors 130 is a multi-axis load cell (which may also measure torque), from which only the measured vertical force is utilized. Typically a bearing 140 will not be utilized with such a multi-axis load cell; rather, a substantially rigid attachment will be utilized in order to transmit forces along the multiple axes. Force sensors 130 generally support platform 110 and are not embedded therein (thus, a subject being measured does not directly contact force sensors 130).

The force sensors 130 are generally disposed at or near the periphery of platform 110 such that a load (e.g., a human subject) on the platform may be measured irrespective of its position on the platform 110. Thus, in most embodiments, no other structure supports the platform 110. In preferred embodiments, at least three non-collinear force sensors 130 are utilized to support platform 110, thereby defining the measurement "plane," but four (as shown in FIG. 1) or even more force sensors 130 may be utilized (Herein, multiple sensors being non-collinear means that all of the sensors do not fall on the same line, while any fewer than the entire number of sensors may do so.) The use of four or more force sensors 130 enables the utilization of a rectangular measurement plane (i.e., with four force sensors 130 at the corners), which facilitates force measurement (all of the forces will be of the same sign when subject 150 is within the rectangular area), thus simplifying the bearing design and enabling use of a wider choice of force sensors 130.

In an embodiment, force sensors 130 may be mounted to platform 110 via a kinematic or quasi-kinematic mount to minimize internal forces or torques due to, e.g., differential thermal expansion of platform 110 or structural deflection of platform 110 or surface 120. As known in the art, a kinematic mount is one in which all six degrees of freedom are singly constrained, thus assuring prevention of movement and non-introduction of stress into the system. Kinematic and quasi-kinematic mountings are further described in M. L. Culpepper, "Design of quasi-kinematic couplings," Precision Engineering, Vol. 28, pp. 338-357 (2004), the entire contents of which are incorporated by reference herein. Generally, quasi-kinematic mounts are preferred for systems having four or more force sensors 130, while systems having three force sensors 130 may utilize kinematic or quasi-kinematic mounts.

During operation of measurement system 100, a human subject 150 is positioned entirely on the platform 110, thus applying his/her full weight to the platform 110 and thus, to force sensors 130. Preferably the subject 150 is substantially vertical, at least above the waist, i.e., at least the heart, lungs, and thorax of subject 150 are substantially vertical. The subject 150 may be instructed to remain fairly still, i.e., to refrain from gross movements or shift locations of his/her feet. Force sensors 130 then measure at least the vertical forces at the location of each force sensor 130, which are generally due to the weight of the subject 150, the weight of platform 110 (and any additional structures thereon, as detailed below with respect to FIGS. 2 and 3), and any additional forces due to motion and/or vibration of subject 150. Such additional forces include forces due to, e.g., cardiac activity, respiratory activity, and/or swaying or shifting of the center of gravity of subject 150. As detailed below, the measured forces are processed and utilized to identify particular physiological and/or behavioral signals from subject 150, e.g., signs of nervousness, anxiety, and/or deception. The subject 150 may be interviewed or subjected to other cognitive stimuli during the measurement of the forces described above. Such interviews or exposure to cognitive stimuli may be intermittent, i.e., may involve multiple spaced-apart questions or exposures such that a baseline reading may be established prior to and/or during the interview or exposure.

The weight and weight distribution of platform 110 are typically constant and known. One or more ancillary sensors may optionally be attached either to the platform itself, or to the supporting surface in the proximity of the platform. For example, one or more side-contact sensors 160 may be placed on one or more of the sides of the platform 110 (or elsewhere) to detect whether some other structure or person is contacting the platform 110, thus degrading the quality and/or accuracy of the signals derived by system 100. One or more tilt or vibration sensors 170 may be placed either on the platform 110 or on the supporting structure 120 near the platform 110, in order to measure tilt or vibrations that may require filtering (or other compensation) to improve the accuracy of the measured signals.

Since the platform 110 is completely supported by the force sensors 130, all of the vertical forces are measurable by the sensors 130; that is, there are no alternative load paths by which any vertical force from the platform 110 or the subject 150 can escape measurement. Consequently, forces due to the entire weight of subject 150 are captured, and there are no portions of platform 110 where portions of the subject's weight might go unmeasured. The individual forces measured by the force sensors 130 may vary depending on the position of subject 150 on the platform 110. For example, if the subject 150 sways while standing on the platform 110, the individual forces will generally vary as functions of time and position. However, the total of the vertical forces measured by the force sensors 130 will generally be independent of the subject's location or horizontal motions. The total of the vertical forces is almost constant—but not exactly constant—due to, e.g., the forces resulting from the action of the heart 180 of the subject 150. Specifically, the total force will typically vary due to the inertial reaction resulting from the pulsating nature of the heartbeat and the elastic nature of the heart and the aortal tissue.

Figure 2:
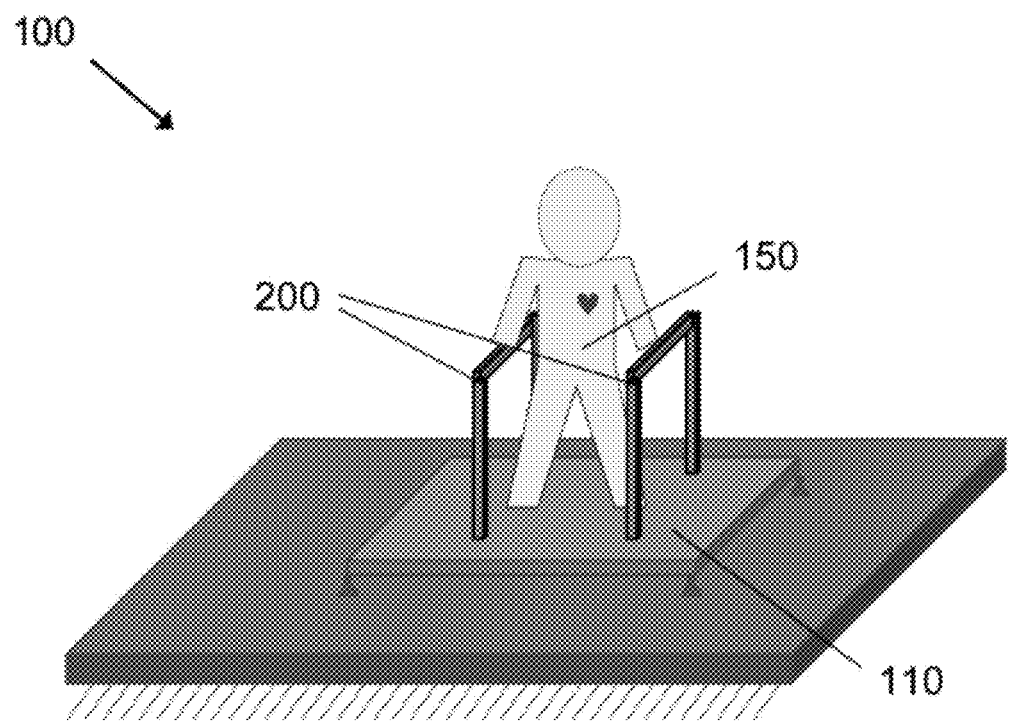

FIG. 2 depicts the measurement system 100 incorporating a support structure 200 (as described above). Thus, during signal acquisition, the subject 150 may not be entirely free-standing. Rather, the subject 150 may steady himself/herself by touching or grasping the support structure 200 (here depicted as two railings) that is located on (and thus supported by) the platform 110. Since the support structure 200 is entirely supported by the platform 110, the entire weight of subject 150 is transmitted to the platform (a portion of the weight through support structure 200), thus enabling the force sensors 130 to measure the entire weight and weight distribution of the subject 150. (The constant additional weight of the support structure 200, which is known, may be compensated for as detailed below.) Support structure 200 is preferably mounted on platform 110 such that it is substantially stationary in a fixed location during signal acquisition from a subject 150. Herein, while a substantially stationary support has a fixed location, it may not be entirely incapable of motion. For example, a support structure 200 may be designed to "wobble" or tilt slightly, thus encouraging the subject 150 not to rest his/her entire weight thereon.

Figure 3:
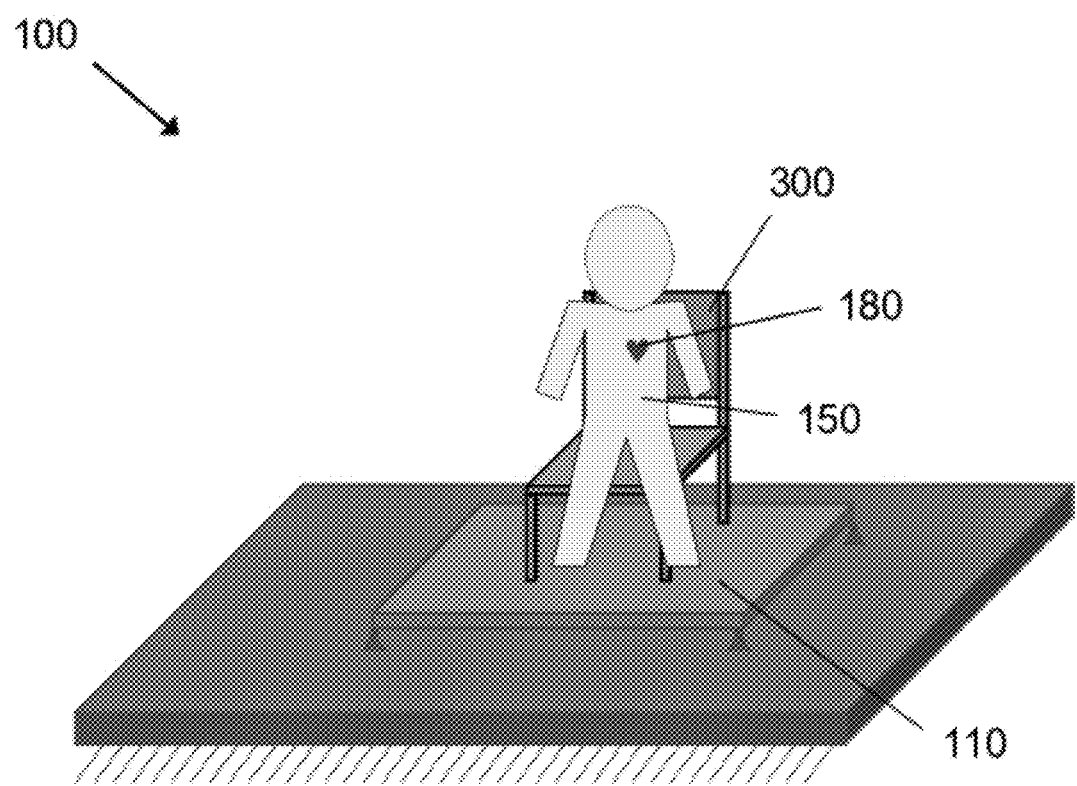

Referring now to FIG. 3, in various embodiments, measurement system 100 includes a chair 300 that is entirely supported by the platform 110. As shown, the subject 150 may be seated in chair 300 during the measurement procedure. The thorax of subject 150 generally remains substantially vertical, such that the heart 180 has substantially the same orientation as in FIGS. 1 and 2. Chair 300 may incorporate multiple legs (as shown in FIG. 3), or may have a single substantially flat base. Chair 300 may not necessarily have a back support, but may rather be a stool or other structure for supporting the entire weight of a seated subject 150. Since, like support structure 200 in FIG. 2, the chair 300 is entirely supported by the platform 110, the entire weight of subject 150 is transmitted, directly or indirectly, to the platform 110. Thus, as detailed above, the force sensors 130 measure the entire weight and weight distribution upon the platform 110 of subject 150. The constant additional weight of the chair (and its distribution among the force sensors 130), which is known, may be compensated for as detailed below. Chair 300 is preferably mounted on platform 110 such that it is stationary in a fixed location during signal acquisition from a subject 150. In some embodiments, chair 300 replaces, rather than supplements, platform 110. Specifically, force sensor(s) 130 directly support the entire weight of chair 300 (and subject 150 sitting thereon) without platform 110 therebetween.

Figure 4:
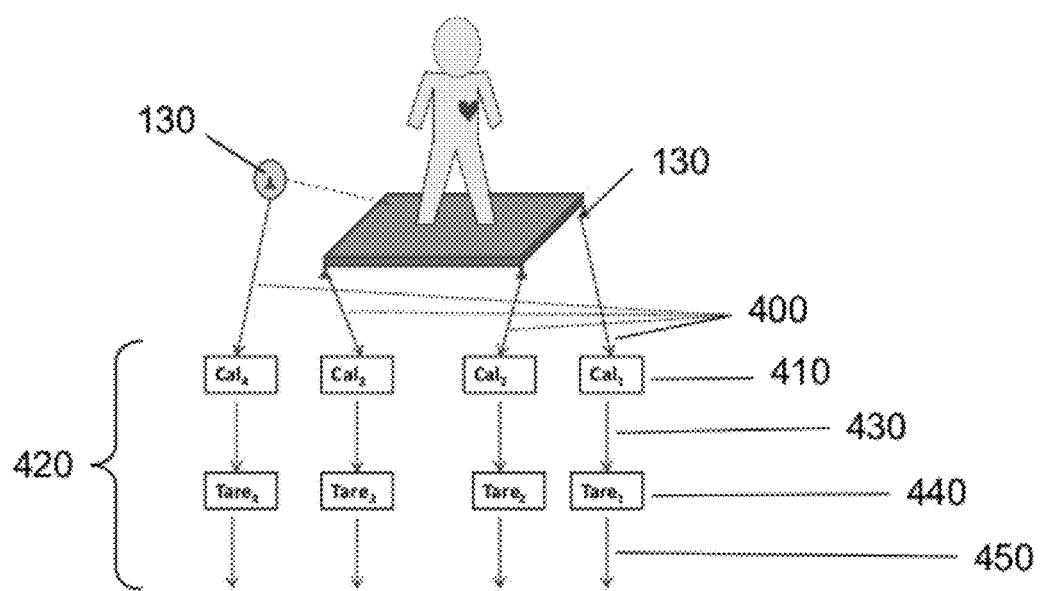
FIGS. 4-6 schematically depict various portions of signal processors for deriving physiological and/or behavioral signals from data measured by a measurement system, as well as flowcharts of the flow of such data, in accordance with embodiments of the invention.
Figure 5:
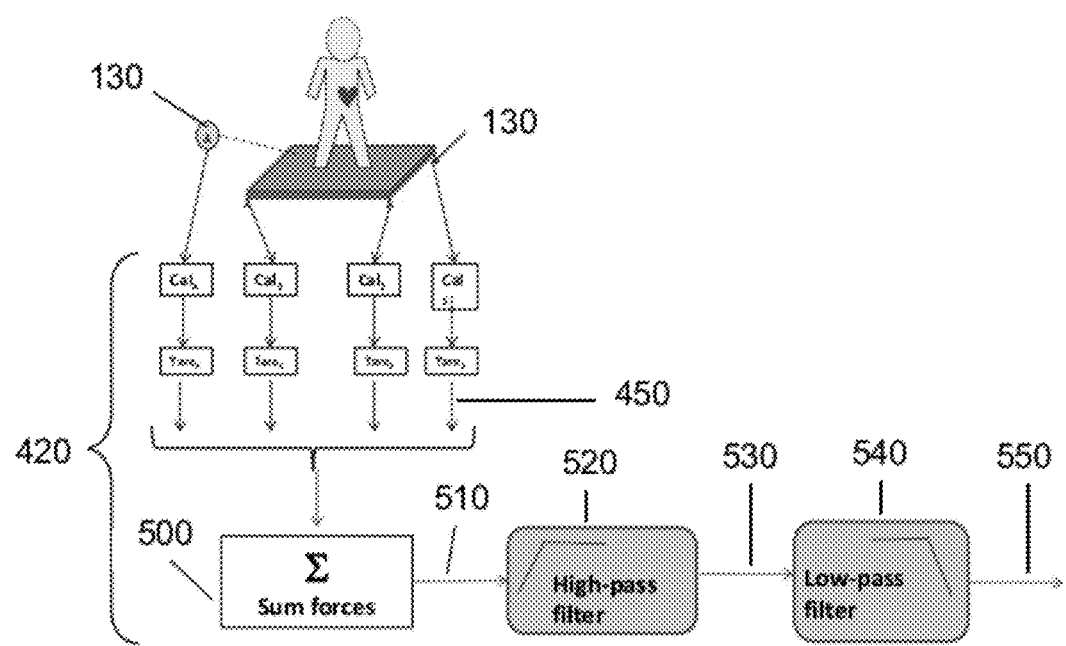
Figure 6:
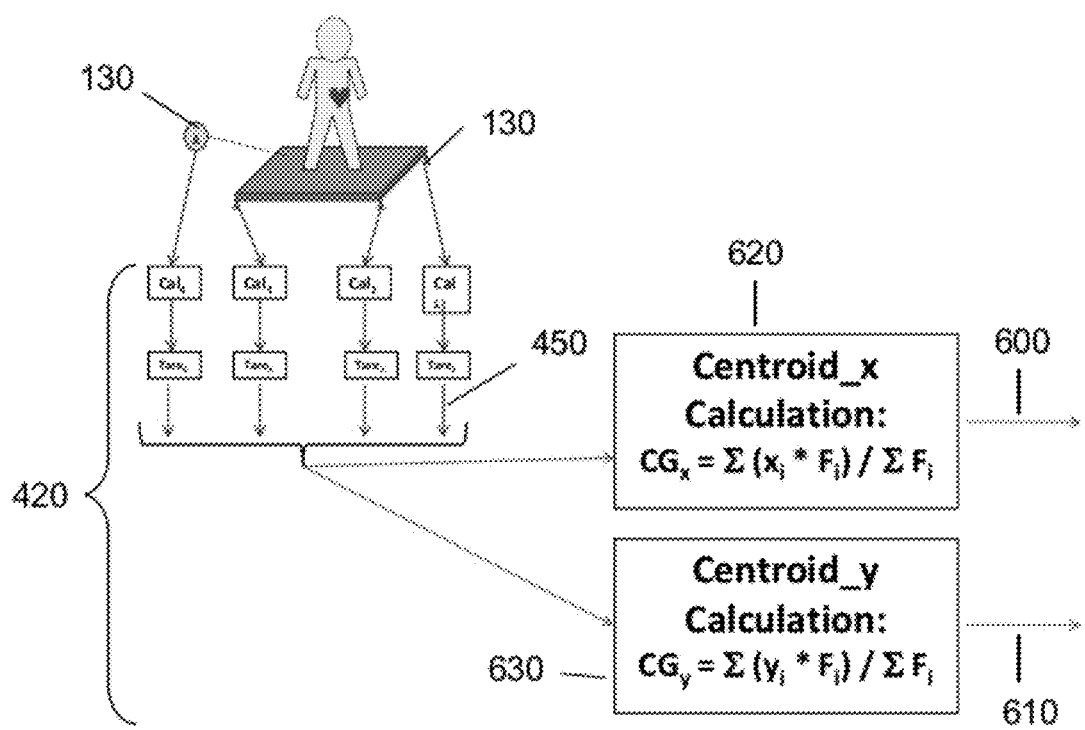

FIGS. 4-6 schematically depict a representative manipulation and processing of the measured signals from the force sensors 130 in order to obtain the desired physiological and/or behavioral signals. In FIG. 4, the raw signals 400 from the force sensors 130 are processed by one or more calibration modules 410 of a signal processor 420. Signal processor 420 (and the modules therein) is in electronic communication with force sensors 130, and may include or consist essentially of, e.g., dedicated analog and/or digital circuitry. (Herein, the term "electronic communication" includes having electrical connections through intervening electronic components, such as computers, as well as wired and wireless, or even optical, connections.) In preferred embodiments, an individual calibration module 410 is associated with and tailored to each force sensor 130. For example, a force sensor 130 may be subjected to known, well-characterized loads, and its output mapped as a function of the known loads. Calibration module 410 incorporates the output map to correct for any peculiarities of the particular force sensor 130. In some embodiments, a single calibration module 410 is utilized for multiple, or even all, of the force sensors 130. Outputs 430 from the calibration modules are the calibrated vertical forces from the force sensors 130, i.e., force quantities substantially free of bias, slope error, hysteresis, and/or non-linearity. In various embodiments, the calibration by calibration module(s) 410 enables the identification and separation of small physiological signals (e.g., the BCG) from other substantially larger variations in the measured forces due to, e.g., sway-induced changes in the location of the center of gravity of subject 150 or variations in the measurement behavior of individual force sensors 130.

Outputs 430 are preferably input into one or more taring modules 440 that subtract therefrom the known weight contributions from the (empty) platform 110 and any fixtures thereon (such as support structure 200 and/or chair 300). The outputs 450 from the taring modules 440 are a set of vertical force signals (also depicted in FIG. 6 as $F_i$), that are due solely to the subject 150 and the subject's motions and vibrations (both external from, e.g., swaying, and internal from, e.g., the heartbeat). In an embodiment, the outputs 430 are processed as detailed below without intermediate taring by taring modules 440.

In FIG. 5, the outputs 450, are further processed by signal processor 420 to produce a physiological or behavioral signal, e.g., the BCG signal. The outputs 450 are summed together by a summation module 500, thus producing a total vertical force signal 510 (also depicted in FIG. 6 as $\Sigma F_i$). The total vertical force signal 510 is typically not constant as a function of time, but varies slightly due to motions or vibrations (internal or external) of subject 150. Among these vibrations is the BCG, which is determined as detailed below.

The total vertical force signal 510 is filtered by a high-pass filtering module 520 that removes both the steady-state (i.e., direct-current or DC) component (i.e., due to the weight of subject 150) and the spectral components that are below the cardiac frequencies of interest, thereby producing the output 530. In various embodiments, the cardiac frequencies of interest range from approximately 0.5 Hz to approximately 50 Hz, and thus include higher frequencies indicative of harmonics and/or overtones of a human heartbeat. The upper range of the cardiac frequencies of interest may, in other embodiments, depend on noise in the measurement system and/or measurements, and may only range to approximately 30 Hz, or even only to approximately 10 Hz.

High-pass filtering module 520 may be implemented in, e.g., analog and/or digital circuitry. High-pass filtering module 520 may utilize a single-pole high-pass filter; however, in preferred embodiments, high-pass filtering module 520 utilizes one or more Bessel filters (or similar linear filters with substantially constant group delay across the passband).

The output 530 is filtered by a low-pass filtering module 540 to remove high-frequency components substantially above the spectral content of, and unrelated to, the action of the heart 180 of subject 150 (such as, e.g., vibrations from nearby ventilation or air-conditioning systems). While herein high-pass filtering module 520 and low-pass filtering module 540 have been described as separate and discrete, in practice they may be combined into a single band-pass filtering module within signal processor 420. The filtering produces a BCG signal 550 that has been band-pass filtered to preferentially pass the spectral components in the cardiac band of interest. In an exemplary embodiment, the BCG signal 550 is a force-based BCG and is an extremely small fraction (e.g., less than 1%, or between approximately 0.02% and approximately 0.3%) of the total weight of subject 150.

Once obtained, BCG signal 550 may be utilized in, e.g., detection of nervousness, anxiety, and/or deception in security screening or surveillance, or even detection of proper and improper cardiac function in medical screening. In many embodiments, BCG signal 550 is determined without reference to, concomitant measurement of, or dependence on any sway of subject 150 (i.e., movements of the subject's center of gravity, as described below). Thus, for example, the BCG signal 550 of a subject 150 attempting to mask signs of anxiety by intentional sway may still be obtained and utilized as a valuable measure of nervousness or deception. And, as described above, BCG signal 550 is obtained without any conventional BCG apparatus or the requirement that subject 150 be oriented horizontally.

In additional embodiments, BCG signal 550 may be analyzed via, e.g., Fourier-transform, time-domain, and/or wavelet-based techniques to produce an average heart rate over a particular time interval or to measure the inter-beat interval (IBI). BCG signal 550 may be utilized to measure the degree of respiratory-sinus arrhythmia (RSA), i.e., variations in heart rate with respiration. Changes in IBI and/or RSA have been correlated with levels of elevated stress and/or deception (see e.g., B. Verschuere et al., "Autonomic and behavioral responding to concealed information: Differentiating orienting and defensive responses," Psychophysiology, vol. 41, pp. 461-466 (2004), and The Polygraph and Lie Detection, National Research Council (2003), the entire contents of both of which are incorporated by reference herein).

System 100 and signal processor 420 may also be utilized to measure sway (in any direction within the plane of surface 110) of the subject 150. In FIG. 6, the outputs 450 are processed, together with the locations of the force sensors 130, to produce two signals 600, 610 indicative of the location of the subject's center of gravity in the horizontal plane, i.e., the x- and y-components of the center of gravity of subject 150 (also respectively depicted in FIG. 6 as $CG_x$ and $CG_y$). The outputs 450 are processed by two centroid-calculating modules 620, 630, together with the locations of the load cells 130, to produce signals 600, 610. In various embodiments, centroid-calculating modules 620, 630 apply the centroid formula (i.e., the ratio of the position-weighted sum of the outputs 450 over the un-weighted sum), together with the respective location data ($x_i$ or $y_i$ respectively, in FIG. 6) of the force sensors 130 to produce signals 600, 610. Once obtained, signals 600, 610 may be utilized in, e.g., detection of nervousness, anxiety, and/or deception in security screening or surveillance, as the relative amount of change in center of gravity is generally related to emotional states such as anxiety or fear. Analysis of signals 600, 610 in the time and frequency domains may enable detection of a "freeze" response, in which a subject becomes more still in response to fear-provoking stimuli. Specifically, a subject will generally shift its center of gravity less during fear-provoking stimuli than during neutral stimuli. In various embodiments, signals 600, 610 may be utilized to detect the degree of nervous jitter or hypervigilance in subject 150.

Although the modules in signal processor 420 have been described separately, this is for clarity of presentation only. As long as signal processor 420 and system 100 perform all necessary functions, it is immaterial how they are distributed therewithin and the programming or hardware architecture thereof. Furthermore, the above-described implementation is exemplary only. Other hardware approaches are possible, e.g., the various modules of embodiments of the invention may be implemented on a general-purpose computer programmed with appropriate software instructions implementing the functions described below, or as hardware circuits (e.g., as an application-specific integrated circuit, or ASIC), analog and/or hybrid analog/digital implementations, or as mixed hardware-software combinations. In various embodiments, system 100 and/or signal processor 420 may include one or more displays for depicting the measured and/or calculated signals, and/or for displaying alerts to users based upon the calculated signals (e.g., if anxiety or deception is detected in a subject). A mass storage device for storage of measured and derived signals may be included, as may additional analysis modules for computation of other physiological or behavioral signals based on the measured data. System 100 may also include, e.g., a keyboard and/or a position-sensing device (e.g., a mouse) to facilitate user interaction therewith.

The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A system for measuring physiological and behavioral signals in a human subject, the system comprising:
    a measurement platform for bearing the subject;
    at least one of a substantially stationary support or a chair disposed entirely on the platform such that an entire weight of the support or chair is supported by the platform;
    at least one force sensor for measuring vertical force imparted by an entire weight of the subject, the at least one force sensor supporting the measurement platform and disposed between the measurement platform and a support surface; and
    a signal processor for deriving at least one physiological or behavioral signal, including a ballistocardiogram, from the measured force.

2. The system of claim 1, wherein the at least one force sensor measures only substantially vertical force.

3. The system of claim 1, further comprising a bearing disposed between each said at least one force sensor and the platform, the bearing substantially transmitting vertical force but not torque from the platform to the force sensor.

4. The system of claim 1, wherein the at least one force sensor comprises at least three non-collinear force sensors disposed proximate a periphery of the platform.

5. The system of claim 1, wherein the signal processor comprises at least one calibration module for calibrating the vertical force, thereby substantially eliminating at least one of bias, slope error, hysteresis, or non-linearity from the vertical force.

6. The system of claim 1, wherein the signal processor comprises at least one taring module for subtracting from the vertical force a weight contribution from the platform.

7. The system of claim 1, wherein (i) the at least one force sensor comprises a plurality of force sensors, and (ii) the signal processor comprises a summation module for summing vertical force measured by each of the force sensors.

8. The system of claim 1, wherein the signal processor comprises a high-pass filtering module for removing a steady-state component from a total vertical force measured by the at least one force sensor.

9. The system of claim 8, wherein the high-pass filtering module removes from the total vertical force a spectral component having a frequency below a cardiac frequency of interest.

10. The system of claim 8, wherein the high-pass filtering module comprises a Bessel filter.

11. The system of claim 1, wherein the signal processor comprises a low-pass filtering module for removing, from a total vertical force measured by the at least one force sensor, a spectral component having a frequency above a cardiac frequency of interest.

12. The system of claim 1, wherein the signal processor comprises a centroid-calculating module for determining a center of gravity of the subject based on the measured force.

13. The system of claim 12, wherein at least one derived physiological or behavioral signal comprises at least one of jitter or hypervigilance.

14. A method for measuring physiological and behavioral signals, the method comprising:
    measuring a vertical force imparted by an entire weight of a human subject having a substantially vertical thorax and disposed upon a measurement platform, the vertical force measured by at least one force sensor that supports the measurement platform and is disposed between the measurement platform and a support surface, at least one of a substantially stationary support or a chair being disposed entirely on the platform such that an entire weight of the support or chair is supported by the platform; and
    extracting at least one physiological or behavioral signal, including a ballistocardiogram, from the measured vertical force.

15. The method of claim 14, wherein the at least one physiological or behavioral signal is extracted without sensors attached to the subject.

16. The method of claim 14, further comprising calibrating the measured vertical force to substantially eliminate at least one of bias, slope error, hysteresis, or non-linearity therefrom.

17. The method of claim 14, further comprising subtracting from the vertical force a weight contribution of the platform.

18. The method of claim 14, wherein extracting the at least one physiological or behavioral signal comprises removing from the measured vertical force at least one spectral component having a frequency above or below a cardiac frequency of interest.

19. The method of claim 14, wherein extracting the at least one physiological or behavioral signal comprises removing from the measured vertical force a steady-state component corresponding to the entire weight of the subject.

20. The method of claim 14, wherein extracting the at least one physiological or behavioral signal comprises determining a center of gravity of the subject.

21. The method of claim 14, wherein at least one extracted physiological or behavioral signal comprises at least one of jitter or hypervigilance.

22. The method of claim 14, wherein the vertical force is measured by a plurality of force sensors disposed proximate a periphery of the platform.

23. The method of claim 14, further comprising at least one of interviewing the subject or subjecting the subject to a cognitive stimulus while measuring the vertical force.

* * * * *